US007062951B2

(12) United States Patent
Ebert

(10) Patent No.: US 7,062,951 B2
(45) Date of Patent: Jun. 20, 2006

(54) METHOD AND DEVICE FOR MEASURING PLASTICITY OF MATERIALS SUCH AS CERAMIC RAW MATERIALS AND MASSES

(75) Inventor: Rolf Ebert, Eckental (DE)

(73) Assignee: Brabender GmbH & Co. KG, Duisburg (DE)

( * ) Notice: Subject to any disclaimer, the term of this patent is extended or adjusted under 35 U.S.C. 154(b) by 0 days.

(21) Appl. No.: 10/823,824

(22) Filed: Apr. 14, 2004

(65) Prior Publication Data
US 2004/0221657 A1   Nov. 11, 2004

(30) Foreign Application Priority Data
May 7, 2003   (DE)   ............... 103 20 578
Jun. 7, 2003   (DE)   ............... 103 25 958

(51) Int. Cl.
*G01M 7/00* (2006.01)
(52) U.S. Cl. .................................... 73/12.04
(58) Field of Classification Search ............. 73/12.04, 73/12.05, 12.06, 12.07, 788, 789, 790, 81, 73/82, 849
See application file for complete search history.

(56) References Cited

U.S. PATENT DOCUMENTS

| 4,249,749 | A | * | 2/1981 | Collier ........................ 280/35 |
| 4,383,450 | A | * | 5/1983 | Pringiers et al. .............. 73/790 |
| 5,739,411 | A | * | 4/1998 | Lee et al. ................... 73/12.13 |
| 6,161,422 | A | * | 12/2000 | Thomas et al. ................ 73/38 |
| 6,609,410 | B1 | * | 8/2003 | Axe et al. .................. 73/12.04 |
| 6,755,087 | B1 | * | 6/2004 | Clegg .................... 73/862.639 |

* cited by examiner

*Primary Examiner*—Max Noori
(74) *Attorney, Agent, or Firm*—Collard & Roe, P.C.

(57) ABSTRACT

A method for measuring the plasticity of materials such as ceramic raw materials and masses. A weight acts on a sample body and a path signal that reproduces the deformation of the sample body is measured. During the deformation process, the time progression of a reaction force applied by the sample body is measured. Path and force measurement values are passed to a computer for processing and evaluation. Devices for measuring the plasticity of a material according to the method are also disclosed.

13 Claims, 4 Drawing Sheets

METHOD AND DEVICE FOR MEASURING PLASTICITY OF MATERIALS SUCH AS CERAMIC RAW MATERIALS AND MASSES

CROSS REFERENCE TO RELATED APPLICATIONS

Applicant claims priority under 35 U.S.C. §119 of GERMAN Application Nos. 103 20 578.0 filed on May 7, 2003 and 103 25 958.9 filed on Jun. 7, 2003.

BACKGROUND OF THE INVENTION

1. Field of the Invention

The invention relates to methods for measuring the plasticity of materials such as ceramic raw materials and masses. Furthermore, the invention relates to a device for implementing such methods.

2. The Prior Art

The term plasticity of a ceramic raw material or a ceramic mass is understood to mean the capacity of the ceramic raw material or mass to deform under the effect of external forces, without losing the cohesiveness of its particles. Another characteristic of plasticity is that irreversible deformation occurs only if the external force has exceeded a minimum value, known as the yield value. Forces below the yield value cause only elastic, reversible deformation.

In the case of clay/water mixtures, plastic deformation is found at water contents of approximately 20 to 25%.

The yield value has a very significant practical importance with respect to ceramics. It prevents an already shaped, but unfired ceramic piece from deforming under its own weight.

Experience has taught that plasticity increases with increasing deformation speed. This effect is utilized in practice by shaping ceramic materials at the highest possible speed.

Methods of Measuring Plasticity

For practical operations, two properties of a plastic mass are generally significant: the force that must be applied for deformation; and the maximum deformation that can be achieved until cracks occur.

The methods of measuring plasticity can be divided into methods in which a variable that is assumed to have a relationship with plasticity is measured; and methods in which an attempt is made to obtain a direct conclusion concerning plasticity.

In the Pfefferkorn method, a plate having a defined weight of 1192 g is dropped from a height of 186 mm, onto a measurement cylinder having a height ($h_o$) of 40 mm and a diameter of 33 mm, whereby compression to height $h_1$ occurs. The water content at which the compression ratio $h_o:h_1=3.3:1$ is considered to be the plasticity number according to the Pfefferkorn method. The water content at which a compression ratio $h_0:h_1=2.5:1$ is reached is referred to as the make-up water requirement.

In the method according to Dietzel, the same equipment used in the Pfefferkorn method is used, however rather than using a high deformation speed, the cylinder is compressed slowly, until cracks form. The compression in percent of the original height is considered to be the measure of plasticity.

In the Atterberg method, which is used internationally by soil scientists, two moisture content values representing limit values of the plastic state and the fluid state are determined. The limit value of the plastic state is the roll-out value, below which a mass can no longer be rolled out into thin strands without becoming crumbly. The limit value of the fluid state is the flow limit, at which a cut into the mass flows together when knocked on. The width of the water content range between these limit values serves as a measure of the plasticity.

Based on the Attenberg method, the plasticity number according to Rieke is considered to be the range between the roll-out limit and the make-up water requirement, which is defined to be the moisture content at which the mass just stops sticking to a person's hands.

According to Cohn, the water content at which a standardized, loaded rod penetrates to a defined depth into the mass within a predetermined time is determined.

Norton and Baudran use a torsion test for determining a measurement number for plasticity. The product of the yield value and the maximum deformation is referred to as "workability." It reaches a maximum at a certain water content.

Haase uses the quotient of tear resistance and deformation pressure as a measure of plasticity. Haase's deliberations proceed from the assumption that a mass is more plastic the greater the cohesion of the particles (tear resistance), but the smaller the forces for reciprocal shifting of the particles, (the lower the viscosity of the mass).

The method according to Hofmann and Linseis is based on a similar consideration. Here, the quotient of the tear resistance and the yield value is used as a measure of plasticity. The yield value is characterized by the press-out pressure at which the mass can be transported through a die.

In the determination of plasticity using the Brabender plastograph, a powder is thoroughly mixed in a kneading chamber at a constantly increasing water content. The torque of the drive motor of the kneading arms, i.e. the resistance of the powder/liquid system to deformation, is measured. The amount of torque at the curve maximum as well as the steepness of the flanks of the maximum are considered to be a measure of the plasticity. Furthermore, the water content at the maximum torque can be derived from the curve.

A cyclical stress test (torsion) is indicated by Ashbury. Here the effective stress varies between maximum values +t and −t with a period duration of approximately 1 min. The results are quite informative for a theoretical discussion of plasticity. The deformation e that occurs is measured and the area of the hysteresis curves is a measure of the deformation work to be exerted.

The informational value and acceptance of the foregoing methods are limited, in part, by a great amount of measurement technology effort and, in part, by limited accuracy and lack of personal neutrality. The elastic properties of the sample are not determined, with the exception of the Brabender plastograph (measurement kneader).

SUMMARY OF THE INVENTION

The invention relates to an improvement over a method of the types stated above, in such a manner that the method is independent of individual assessments and that accuracy of the measurements is improved.

The invention accomplishes this task in that during a deformation process, a time progression of reaction force applied by a sample body is measured and that path and force measurement values are passed to a computer for processing and evaluation.

Therefore, there is presented a new, significantly expanded method based on the Pfefferkorn method, which takes elastic properties into consideration. This method not only makes an end point of a measurement process available as a result, by means of representing the results, but also makes an entire sequence of the deformation visible. This sequence starts with a high deformation speed, and thereby allows a much more extensive characterization of plastic material properties.

In a method according to an embodiment of the invention a sample body is deformed by impacting the sample body with a weight. A weight may be dropped from a predetermined height onto a sample body. The weight may impact the sample body in a free fall or at a controlled or regulated speed.

A movement of the impacting weight is measured over time during a deformation of the sample body. A path signal which is proportional to a deformation of the sample body is generated based on a movement of the weight.

A reaction force of the sample body is measured over time during the deformation of the sample body. A force signal which is proportional to the reaction force is generated and the path signal and force signal are processed and evaluated with a computer.

The new method that relates to the invention accomplishes the aforementioned task by means of a device with which the method indicated above is carried out.

The device may consist of a guided drop weight (for example, having a weight of 1192 g, as in the Pfefferkorn method), which may drop from an adjustable height (for example between 100 and 200 mm) onto a sample which is normally cylindrical.

A guide guides the weight which impacts the sample body. The guide may be linear and may comprise a lever which is rotatable around an axis of rotation. The axis of rotation of the lever may be adjustable in height. A guide may also comprise a parallelogram or scissors system.

The drop weight compresses the sample, for example, to approximately ⅓ of its original height. The sample may stand on a force measurement unit or device, for example a load cell, for measuring a reaction force of the sample body during deformation. This load cell can be resilient in itself or, alternatively, not resilient in itself but mounted on a separate spring system having a path transducer.

A path sensor detects a movement of the weight during a deformation of the sample body. A path signal, which is proportional to a deformation of the sample body, and a force signal, which is proportional to a reaction force of the sample body, are generated, measured and evaluated. A computer may be coupled to the force measurement device and path sensor.

BRIEF DESCRIPTION OF THE DRAWINGS

Other benefits and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENTS

Figure 1:
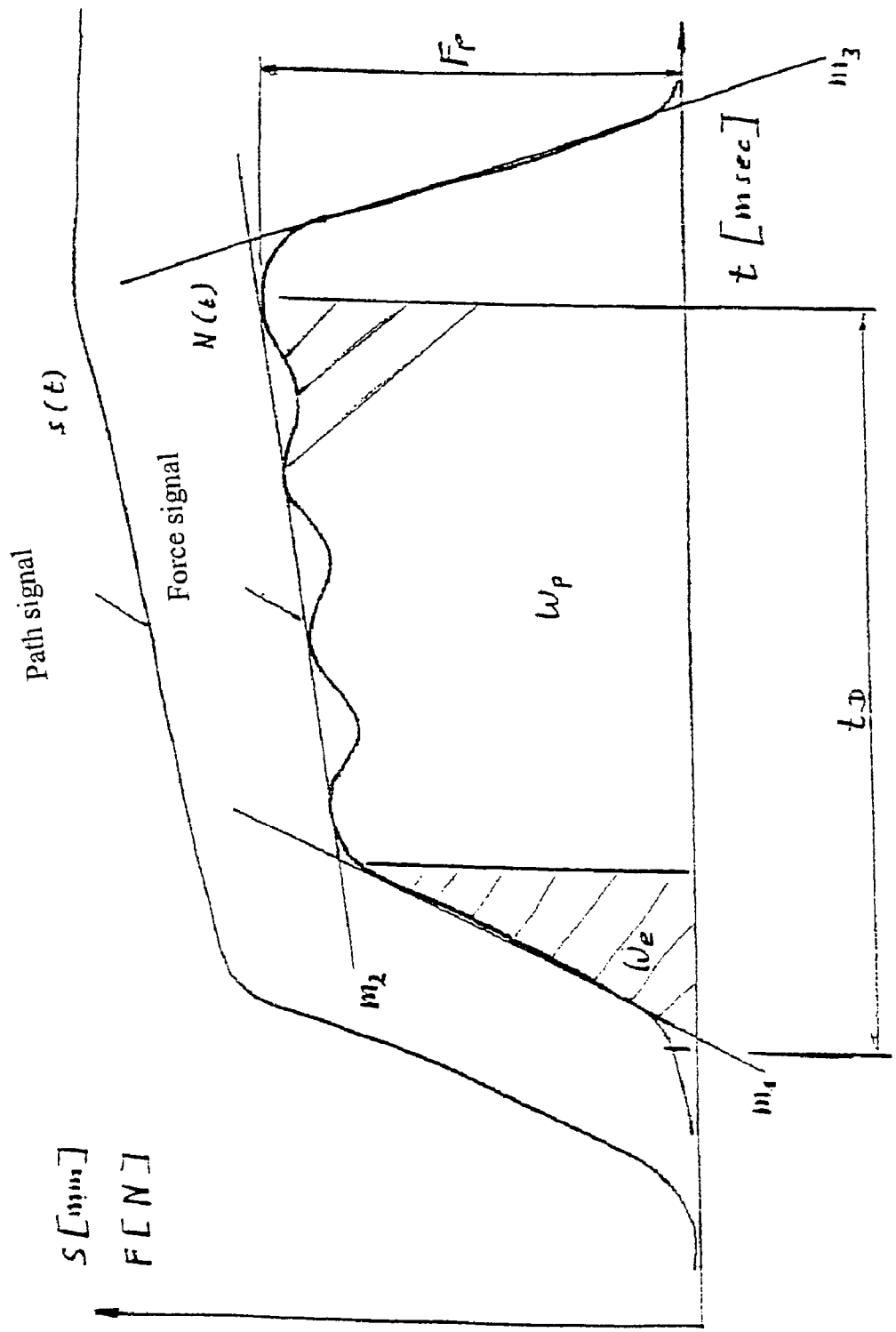
FIG. 1 shows a diagram of a typical progression of measurement values for a path measurement and for a force measurement.

FIG. 1 shows a typical progression of measurement values, for one thing that of the path measurement, and for another that of the force measurement.

In this diagram, the symbols mean:
$t_D$ deformation time (ms)
$F_p$ peak/force signal (N)
s deformation (mm)
$W_e$ elastic deformation energy (Nmm)
$W_p$ plastic deformation energy (Nmm)
$m_1$ increase in force (elastic)(N/ms)
$m_2$ increase in force (plastic)(N/ms)
$m_3$ drop in force signal (N/ms)

As is evident from this diagram, an initial deformation has a high speed and then makes a transition into a deformation having a lower speed, and finally ends at a final deformation (horizontal region).

The force measurement shows, initially, as a function of the yield value of the sample, a more or less great increase in force, which causes the elastic deformation. The force signal progression makes a transition into a more or less wave-shaped increase with a slight incline after an approximately linear increase, depending on the damping behavior of the sample. This range represents plastic deformation.

An incline $m_1$ indicates an elastic force increase, and an incline $m_2$ indicates a plastic force increase.

An area below a linear increase $w_e$ indicates elastic deformation energy, and an area below wave-shaped curve $w_p$ indicates a plastic deformation energy.

Measurements may be taken over a period of time $t_D$, which is referred to as a deformation time, and may be measured in milliseconds.

An absolute maximum of a force signal curve, $F_p$, indicates a maximum force in effect, after which the force returns to zero in a region $m_3$ that decreases in a linear manner.

The signal progression at a load cell results from an impulse of a drop weight and models the plastic and elastic properties of the sample material. Characteristic features of the plastic behavior of a sample can be directly read from a curve progression. The signal contains information about plastic properties of samples in the form of damping behavior and impulse passage through sample material. In addition, a force measurement transducer may be excited to vibrate by means of an impact, and these vibrations may be superimposed on a force signal. The degree of these vibrations may be influenced by: measurement range and resilience properties of a measurement transducer; hardness of a sample; and damping behavior, i.e. elastic properties of a sample material.

Processing software can be used to interpret the curve progression and make numerical values available, which characterize the plasticity of a sample material. A tolerance range, which can be used for an automated "pass-fail" decision can be placed over the signal progression.

A guide of the drop weight may be a linear guide, in which the drop weight drops onto the sample in free fall or under compulsory control, at a constant, accelerated, delayed or oscillating speed.

The drop weight may also be moved on a long lever, about an axis of rotation. The axis of rotation may be adjustable in height.

The guide may also be a long lever having a parallelogram guide, or a scissors system.

A path sensor that measures relative or absolute values, or an angle sensor that works in a similar way with a lever system, may be used for detecting a signal. Any path or angle sensor known in the art, for example potentiometers, Hall effect sensors, optical sensors or incremental sensors may be used for detecting or measuring a signal.

Figure 2:
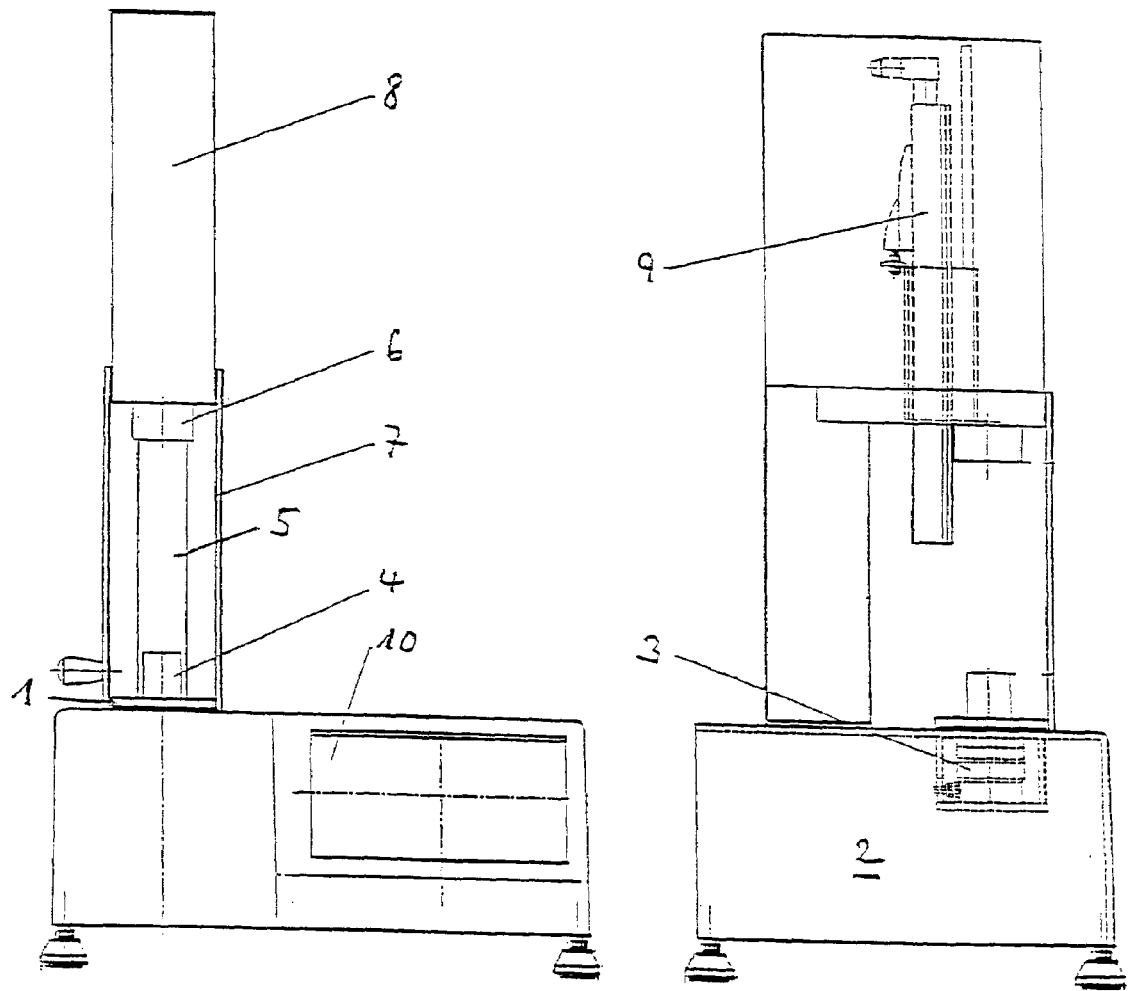
FIG. 2 shows a device according to an embodiment of the invention, specifically in both a side view and a front view.

FIG. 2 shows a device, according to an embodiment of the invention in both a side view and a front view.

A sample body 4 made of a ceramic mass is arranged on a plate 1 that sits on a load cell 3 which is mounted in a housing 2. A guide 5 for a drop weight 6, is disposed vertically above sample body 4. Guide 5 and drop weight 6 are located in a housing comprising a protective hood 7 and an upper hood 8. A path sensor 9 for detecting a movement of drop weight 6 is arranged in an upper hood 8.

A computer to which measurement values of path sensor 9, and/or of load cell 3, are passed and processed is located in lower housing 2. A result, for example as shown in FIG. 1, may be displayed on a screen 10.

Figure 3:
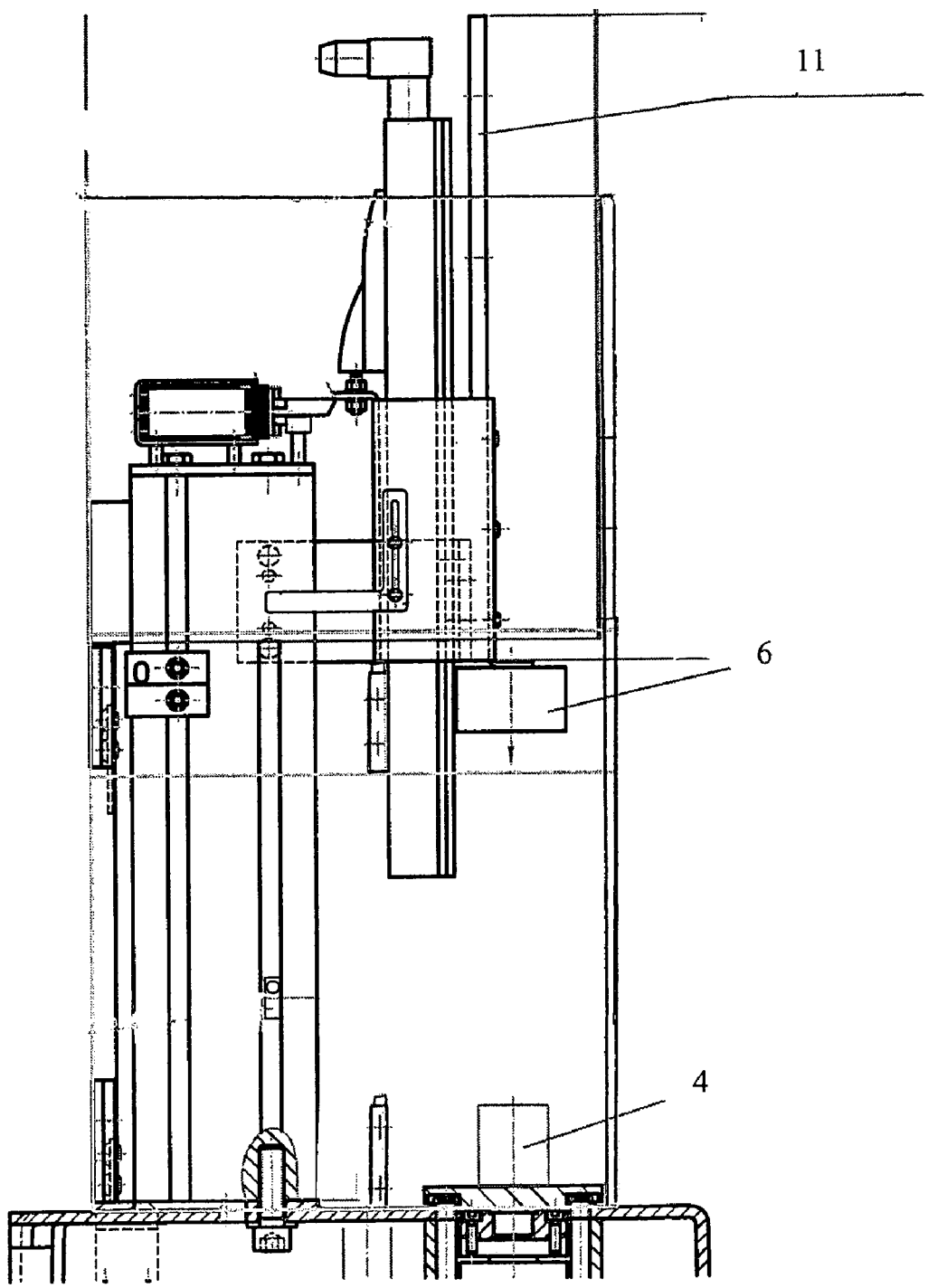
FIG. 3 shows a front view of a device according to an embodiment of the invention.
Figure 4:
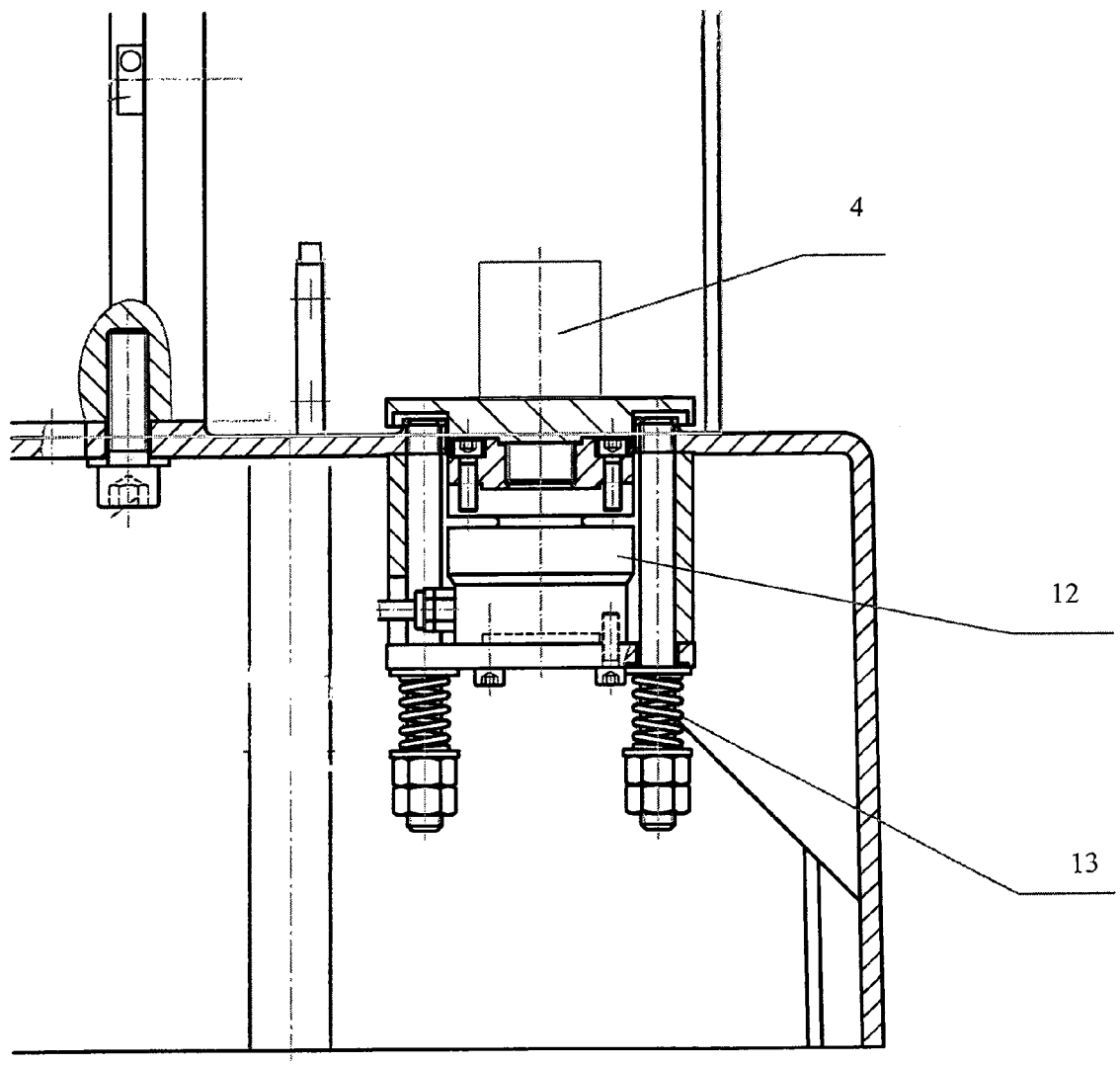
FIG. 4 shows a front view of a portion of a device according to an embodiment of the invention.

As shown in FIG. 3, a guide for drop weight 6 may comprise a linear guide 11. As shown in FIG. 4, the load cell may further comprise a transducer 12, such as a force transducer, and the load cell may be mounted on a separate spring system 13.

In a preferred embodiment, the weight of a drop weight may be 1192 g. A drop height may be adjustable between 100 and 200 mm.

A benefit of the method according to the invention is that the entire sequence of sample deformation may be observed and evaluated, wherein in prior methods only a measurement endpoint is obtained as a result. Another benefit of the method according to the invention is that both elastic and plastic properties of the sample body may be considered. A further benefit of the method according to the invention is that a high deformation speed may be used which allows a extensive characterization of plastic material properties. A further benefit of the method according to the invention is that the method is less susceptible to error from individual assessments and offers greater measurement accuracy that other methods of measuring plasticity of ceramic raw materials or masses.

Accordingly, while at least one embodiment of the present invention has been shown and described, it is obvious that many changes and modifications may be made thereunto without departing from the spirit and scope of the invention.

What is claimed is:

1. A method for measuring a plasticity of a material such as a ceramic raw material or mass, the method comprising the steps of:
   (a) setting a sample body on a force measurement device comprising a force transducer adapted to vibrate upon an impact;
   (b) deforming said sample body by impacting said sample body with a weight, wherein said impacting causes said force transducer to produce a vibration;
   (c) measuring a movement of said weight over time during a deformation of said sample body until an end of said deformation;
   (d) generating a path signal based on said movement of said weight, wherein said path signal is proportional to said deformation of said sample body;
   (e) measuring a reaction force of said sample body over time during said deformation of said sample body until said end of said deformation;
   (f) generating a force signal, wherein said force signal is proportional to said reaction force;
   (g) superimposing said vibration of said force transducer onto said force signal;
   (h) detecting a damping behavior of said vibration by said sample body; and
   (i) processing and evaluating said path signal and said force signal with a computer.

2. The method according to claim 1, further comprising the step of dropping said weight onto said sample body from a pre-determined height.

3. The method according to claim 2, wherein said weight impacts said sample body in a free fall.

4. The method according to claim 1, wherein said weight impacts said sample body at a regulated speed.

5. A device for measuring a plasticity of a material such as a ceramic raw material or mass by impacting and deforming a sample body with a weight and measuring a movement of the weight and a reaction force of the sample body over time during a deformation of the sample body, the device comprising:
   (a) a force measurement device for measuring the reaction force of the sample body during the deformation, wherein said force measurement device is adapted to vibrate upon an impact;
   (b) a sample table disposed on said force measurement device;
   (c) a guide disposed above said sample table wherein said guide is for guiding the weight which impacts the sample body; and
   (d) a path sensor for detecting a movement of the weight;
   wherein a path signal which is proportional to the deformation of the sample body is generated based on the movement of the weight, a force signal which is proportional to the reaction force is generated, a vibration of said force measurement device is superimposed onto said force signal, a damping behavior of said vibration is detected by the sample body, and said path signal and said force signal are measured until an end of the deformation and evaluated.

6. The device according to claim 5, further comprising a computer coupled to said force measurement device and said path sensor.

7. The device according to claim 5, wherein said force measurement device comprises a load cell.

8. The device according to claim 7, wherein said load cell is inherently resilient.

9. The device according to claim 7, further comprising a separate spring system comprising a transducer, wherein said load cell is mounted on said separate spring system.

10. The device according to claim 5, wherein said guide comprises a linear guide.

11. The device according to claim 5, wherein said guide comprises a lever, wherein the weight is disposed on said lever and said lever is rotatable about an axis of rotation.

12. The device according to claim 11, wherein a height of said axis of rotation is adjustable.

13. The device according to claim 5, wherein said guide comprises a lever having a parallelogram guide.

* * * * *